(12) United States Patent
Trupke et al.

(10) Patent No.: US 9,103,792 B2
(45) Date of Patent: Aug. 11, 2015

(54) WAFER IMAGING AND PROCESSING METHOD AND APPARATUS

(75) Inventors: Thorsten Trupke, Coogee (AU); Robert A. Bardos, North Bondi (AU)

(73) Assignee: BT IMAGING PTY LTD., New South Wales (AU)

( * ) Notice: Subject to any disclaimer, the term of this patent is extended or adjusted under 35 U.S.C. 154(b) by 479 days.

(21) Appl. No.: 12/935,654

(22) PCT Filed: Mar. 31, 2009

(86) PCT No.: PCT/AU2009/000396
§ 371 (c)(1),
(2), (4) Date: Sep. 30, 2010

(87) PCT Pub. No.: WO2009/121133
PCT Pub. Date: Oct. 8, 2009

(65) Prior Publication Data
US 2011/0025839 A1    Feb. 3, 2011

(30) Foreign Application Priority Data

Mar. 31, 2008  (AU) ................. 2008901552

(51) Int. Cl.
*H04N 1/04* (2006.01)
*H04N 7/18* (2006.01)
(Continued)

(52) U.S. Cl.
CPC ........ *G01N 21/6489* (2013.01); *G01N 21/9505* (2013.01); *G06T 7/0004* (2013.01); *H01L 22/12* (2013.01); *H01L 31/18* (2013.01); *G01N 2021/646* (2013.01);
(Continued)

(58) Field of Classification Search
CPC . H05K 13/08; H05K 13/0413; G01R 31/309; H01L 21/681; G06T 7/001

USPC .......................................... 348/87; 356/302
See application file for complete search history.

(56) References Cited

U.S. PATENT DOCUMENTS

| 5,006,717 | A  | * | 4/1991 | Tsutsu et al. ............... 250/484.2 |
| 2004/0092042 | A1 | | 5/2004 | Higgs |

(Continued)

FOREIGN PATENT DOCUMENTS

| EP | 1 840 541 A1 | 10/2007 |
| JP | 08-139196 | 5/1996 |

(Continued)

OTHER PUBLICATIONS

Search Report—Intellectual Property Office of Singapore; Application No. 201007119-9, mailed Jul. 19, 2012.
European Search Report including Supplementary European Search Report and European Search Opinion, International Patent Application No. PCT/AU2009/000396, dated May 29, 2012.
M. Abbott et al., "Application of Photoluminescence characterization to the development and manufacturing of high-efficiency silicon solar cells", Journal of Applied Physics, American Institute of Physics, New York, USA, vol. 100, No. 11, Dec. 12, 2006, pp. 114514-1-11 4514-10.

(Continued)

*Primary Examiner* — Jessica M. Prince
*Assistant Examiner* — On S Mung
(74) *Attorney, Agent, or Firm* — Mattinly & Malur, PC (57) ABSTRACT

A method is disclosed whereby luminescence images are captured from as-cut or partially processed bandgap materials such as multicrystalline silicon wafers. These images are then processed to provide information is then utilized to predict various key parameters of a solar cell manufactured from the bandgap material, such as open circuit voltage and short circuit current. The information may also be utilized to apply a classification to the bandgap material. The methods can also be used to adjust or assess the effect of additional processing steps, such as annealing, intended to reduce the density of defects in the bandgap materials.

20 Claims, 10 Drawing Sheets

(51) Int. Cl.
*H04N 9/47* (2006.01)
*G01N 21/64* (2006.01)
*G01N 21/95* (2006.01)
*G06T 7/00* (2006.01)
*H01L 21/66* (2006.01)
*H01L 31/18* (2006.01)
*H02S 50/10* (2014.01)

(52) U.S. Cl.
CPC ........... *G06T 2207/30148* (2013.01); *H01L 2924/0002* (2013.01); *H02S 50/10* (2014.12)

(56) References Cited

U.S. PATENT DOCUMENTS

| | | | |
|---|---|---|---|
| 2005/0196882 A1* | 9/2005 | Steeples | 438/16 |
| 2005/0252545 A1* | 11/2005 | Nowlan et al. | 136/290 |
| 2006/0262296 A1 | 11/2006 | Higgs | |
| 2006/0267007 A1 | 11/2006 | Salzman et al. | |
| 2007/0018192 A1* | 1/2007 | Salzman et al. | 257/103 |
| 2008/0088829 A1* | 4/2008 | Fuyuki | 356/230 |

FOREIGN PATENT DOCUMENTS

| | | |
|---|---|---|
| JP | 2003-324136 A | 11/2003 |
| JP | 2007-251004 | 9/2007 |
| KR | 10-2007-0065727 A | 6/2007 |
| WO | WO 2004/008118 A1 | 1/2004 |
| WO | WO 2007/041758 A1 | 4/2007 |
| WO | WO 2007/128060 A1 | 11/2007 |
| WO | WO 2009/026661 A1 | 3/2009 |

OTHER PUBLICATIONS

Liao et al., "A Comprehensive Study of Indium Implantation-Induced Damage in Deep Submicrometer nMOSFET: Device Characterization and Damage Assessment"; IEEE Transactions on Electron Devices, vol. 49, No. 12, pp. 2254-2262, Dec. 2002.

Fuyuki et al., "Photographic Surveying of Minority Carrier Diffusion Length in Polycrystalline Silicon Solar Cells by Electroluminescence"; Applied Physics Letters 86, 262108 (2005), 3 pages.

Trupke et al., "Photoluminescence Imaging of Silicon Wafers"; Applied Physics Letter 89, 044107 (2006), 3 pages.

Siegelin et al., "Dislocation Related Leakage in Advanced CMOS Devices"; Proceedings of the 31$^{st}$ International Symposium for Testing and Failure Analysis; Nov. 6-10, 2005, McEnery Convention Center, San Jose, California, USA; pp. 59-63.

Niedernostheide et al., "Analysis of Radiation-Induced Defects and Performance Conditioning in High-Power Devices"; Journal of the Electrochemical Society, 150(1) G16-G21 (2003); pp. G15-G21.

International Search Report, International Patent Application No. PCT/AU2009/000396, dated Oct. 8, 2009.

International Preliminary Report on Patentability, International Patent Application No. PCT/AU2009/000396, issued on Oct. 5, 2010.

Trupke et al., "Progress With Luminescence Imaging fo the Characterisation of Silicon Wafers and Solar Cells", 22$^{nd}$ European Photovoltaic Solar Energy Conference, Milan, Sep. 2007.

* cited by examiner

WAFER IMAGING AND PROCESSING METHOD AND APPARATUS

FIELD OF THE INVENTION

The present invention relates to the field of processing luminescence images acquired from direct and indirect bandgap semiconductor materials such as silicon wafers. In particular it relates to methods and apparatus for analysing luminescence images of wafers to obtain information about defects in the wafer material. This information may be used to classify the wafers or to predict operational characteristics of devices made from them.

BACKGROUND OF THE INVENTION

Any discussion of the prior art throughout the specification should in no way be considered as an admission that such prior art is widely known or forms part of common general knowledge in the field.

Most commercial photovoltaic cells (in particular solar cells) today are made from typically 10×10 $cm^2$ up to 21×21 $cm^2$ multicrystalline (mc) silicon wafers which are cut from a cast multicrystalline silicon block. The main processing steps on forming a solar cell after cutting the silicon wafer in the most widely adopted screen printed solar cell process are: 1) surface damage etch, 2) texturing, 3) diffusion, 4) SiN deposition, 5) screen printing of metal contacts, 6) firing, 7) edge isolation, and 8) electrical characterisation and binning. More sophisticated solar cell concepts use so-called selective emitter structures in which highly doped local areas are formed under metal contacts. Other advanced cell concepts use point contacts on the rear to improve the rear surface recombination. Normally, the electrical performance of a cell is measured only towards or at the end of the production process.

The initial wafers are normally produced by sawing a large cast silicon block (also known as an ingot, typically up to 1×1×0.7 $m^3$ in size) into square (10×10 $cm^2$ up to 21×21 $cm^2$) shaped columns (also known as bricks), which are then wire sawn into individual wafers (each typically 150-300 μm thick). Currently, some wafer manufacturers use minority carrier lifetime measurements such as quasi steady state photoconductance or photoconductance decay measurements along the edge of the square block or brick to obtain information about the local material quality. One or several line-scans within the wafer area of individual wafers can also be used to assess the wafer quality. Normally, only limited two-dimensional information about lateral variations of the material quality within each wafer is obtained. This is as a result of a high volume solar cell production line typically handling 1 wafer every one to three seconds, which limits the time available for characterisation.

Some individual solar cell manufacturing processes such as screen printing and firing of electrical contacts can be performed as actual in-line processes, where the partially processed wafers are transported through the process one by one, typically on a belt. Other processes such as diffusion and SiN deposition are often carried out as batch processes with tens or hundreds of wafers being processed simultaneously.

The average throughput of a typical silicon solar cell production line may be one solar cell every one to three seconds, which limits the time available for in-line characterisation of each sample. Existing spatially resolved measurements are generally too slow to yield high resolution two-dimensional information about the electronic wafer quality in such short timeframes. On the other hand it is known that small defects can have a large impact on device performance. High spatial resolution (<1 mm per pixel) is thus required for a reliable characterisation. Manufacturers thus have limited tools that allow them to characterise the electronic properties of every wafer or of even a large fraction of wafers going through a production process with sufficiently high lateral spatial resolution.

Certain materials that emit luminescence have a gap in their electronic density of states, the so-called bandgap. Such materials are referred to as bandgap materials. Direct and indirect bandgap semiconductors, including silicon, are included in this definition. Dislocations are a common type of structural defect in semiconductors such as silicon, and their presence strongly affects the electronic properties of the materials and consequently the performance of devices such as solar cells manufactured from them.

SUMMARY OF THE INVENTION

It is an object of the present invention to overcome or ameliorate at least one of the disadvantages of the prior art, or to provide a useful alternative.

In accordance with a first aspect, the present invention provides a method of conducting an analysis of a bandgap material, said method including the steps of:
  (a) capturing a luminescence image of said bandgap material;
  (b) processing said image to obtain information about defects in said bandgap material; and
  (c) utilising said information to apply a classification to said bandgap material.

In a second aspect, the present invention provides method of conducting an analysis of a bandgap material, said method including the steps of:
  (a) obtaining information about dislocation defects in said bandgap material; and
  (b) utilising said information to apply a classification to said bandgap material.

In accordance with a third aspect of the present invention, there is provided a method of predicting one or more operational characteristics of a device fabricated from a bandgap material, said method including the steps of
  (a) obtaining at least one sample of said bandgap material;
  (b) capturing luminescence image of said at least one sample;
  (c) processing said image to obtain information about defects in said bandgap material from said sample;
  (d) analysing one or more operational characteristics of a device fabricated from said sample; and
  (e) correlating said operational characteristics with said information, wherein
    (i) steps (b) and (c) are repeated for further samples of said bandgap material to obtain further information about the defects in said further samples; and
    (ii) said further information is utilised to predict operational characteristics of devices fabricated from said further samples.

Preferably, the processing of the image includes enhancing the image by any suitable technique known in the art.

The information obtained preferably includes information about dislocation defects of the substrate material. More preferably, the information includes a measure of the density of dislocation defects across the material.

The processing of the image may include determining an absolute or relative area average of the dislocation density or a metric that is correlated with the dislocation density. The processing may also include a weighting function based on the position of the dislocation in relation for example to the metal contacts of a solar cell. The processing may also include a weighting function of the severity of a defect as apparent, for example, in its impact on the effective minority carrier lifetime.

The bandgap substrate material can comprise silicon. In one embodiment, the bandgap substrate material can comprise a multicrystalline silicon wafer and the step (c) can preferably include determining the likely operational characteristics of semiconductor devices which utilise the silicon wafer material as their substrate. In another embodiment, the bandgap substrate material can comprise a cast monocrystalline silicon wafer.

The silicon wafer can be an as-cut unprocessed silicon wafer or a partially processed silicon wafer.

The semiconductor device can comprise a photovoltaic cell.

The image processing can comprise the step of normalising the image with respect to the background doping concentration.

Specific defects, particularly dislocations, often appear with very similar spatial distribution in wafers from nearby regions in the same brick, in other words, the spatial distribution varies very little between several neighbour wafers. The embodiments can also include the step of performing the method on a single or on multiple wafers cut from adjacent or nearby slices of a silicon block or silicon brick and interpolating or extrapolating the results to determine the likely operational characteristics of devices made on other adjacent or nearby wafers. This may allow performance predictions on a larger sample set from measurements on only a subset of samples.

The method can also include the step of locating low material quality regions caused by edge defects or impurities along an edge of the wafer material.

The method can further include the step of: (d) utilising the results of the analysis step to alter parameters associated with a series of processing steps in the formation of a solar cell so as to improve the quality of the solar cell. The parameters can include the conditions for firing a metal pattern into the silicon wafer. The parameters can also include the diffusion conditions for diffusing materials into the silicon wafer.

In certain embodiments, the parameters include the diffusion conditions for diffusing material in to said bandgap material, or parameters for any other process that creates doped regions in said material.

In alternative embodiments, the method can also include the step of normalising the photoluminescence images with respect to the background doping of the wafer. The normalising step consists of dividing the luminescence intensity in each pixel by the background doping concentration.

In other embodiments, the processing can include various options including weighting the area sum or area average of dislocation densities or relative distribution of dislocation density for the location of said dislocation defect relative to the gridlines or metal contacts of a voltaic cell and/or according to the severity of the dislocation defects.

The information can be obtained using photoluminescence, microwave photoconductants decaying, optical transmission or optical reflection measurements. In some cases where optical transmission or optical reflection measurements are used, it is conducted in the 1,400 nm-1,700 nm spectral range.

As discussed below, the abovementioned methods are suitable for a range of to bandgap materials and devices but are preferably designed to predict the operational characteristics of a photovoltaic cell including open circuit voltage, short circuit density, fill factor or efficiency.

In accordance with a fourth aspect of the present invention, there is provided a method of predicting one or more operational characteristics of a device fabricated from a bandgap material, said method including the steps of:
(a) obtaining at least one sample of said bandgap material;
(b) obtaining information about dislocation defects in said at least one sample;
(c) analysing one or more operational characteristics of a device fabricated from said at least one sample; and
(d) correlating said operational characteristics with said information, wherein
  (i) step (b) is repeated for further samples of said bandgap material to obtain further information about dislocation defects in said further samples; and
  (ii) said further information is utilised to predict said operational characteristics of devices fabricated from said further samples.

In accordance with a fifth aspect of the present invention, there is provided a method of predicting one or more operational characteristics of a device fabricated from a bandgap material, said method including the steps of:
(a) obtaining at least one sample of said bandgap material;
(b) obtaining information about dislocation defects in said at least one sample;
(c) utilising said information to apply a classification to said bandgap material;
(d) analysing one or more operational characteristics of a device fabricated from said at least one sample; and
(e) correlating said operational characteristics with said classification wherein
  (i) steps (b) and (c) are repeated for further samples of said bandgap material to obtain a further classification for each of said further samples; and
  (ii) said further classification is utilised to predict said operational characteristics of the devices fabricated from said further samples.

In the preferred embodiments the classification can also be used to reject, price and/or bin the bandgap material into different quality categories, or predict the operational characteristics of devices fabricated from said bandgap material.

A sixth aspect of the present invention provides a method of conducting an analysis of a silicon wafer material, said method including the steps of:
(a) capturing a photoluminescence image of said silicon wafer material;
(b) processing said image to obtain information about defects in said material; and
(c) utilising said information to apply a classification to said silicon wafer material.

In a seventh aspect, the present invention provides a method of predicting one or more operational characteristics of a device fabricated from a silicon wafer, said method including the steps of:
(a) obtaining at least one silicon wafer sample;
(b) capturing a luminescence image of said at least one sample;
(c) processing said image to obtain information about defects in said at least one sample;
(d) analysing one or more operational characteristics of a device fabricated from said at least one sample; and
(e) correlating said operational characteristics with said information, wherein
  (i) steps (b) and (c) are repeated for further silicon wafer samples to obtain further information about the defects in said further samples; and (ii) said further information is utilised to predict the operational characteristics of devices fabricated from said further samples.

In an eighth aspect, the present invention provides a system for conducting an analysis of a bandgap material, said system including:
an image capture device for capturing a luminescence image of said bandgap material;
an image processor for processing said image to obtain information about defects in said material, and;
a classifier for utilising said information to apply a classification to said bandgap material.

In a ninth aspect, the present invention provides a system for conducting an analysis of a bandgap material, said system including:
an acquisition device for obtaining information about dislocation defects in said bandgap material; and
a classifier for utilising said information to apply a classification to said bandgap material.

In a tenth aspect, the present invention provides a system for predicting one or more operational characteristics of a device fabricated from a bandgap material, said system including:
(a) an image capture device for capturing luminescence images of at least one is sample of said bandgap material;
(b) an image processor for obtaining information about defects in said at least one sample;
(c) an analyser for analysing one or more operational characteristics of a device fabricated from said at least one sample;
(d) a correlator for obtaining a correlation between said operational characteristics and said information; and
(e) a predictor for predicting the operational characteristics of devices fabricated from further samples of said bandgap material, based on said correlation and on information about said defects obtained from said further samples.

In an eleventh aspect, the present invention provides a system for predicting one or more operational characteristics of a device fabricated from a bandgap material, said system including:
(a) an acquisition device for obtaining information about dislocation defects in at least one sample of said bandgap material;
(b) an analyser for analysing one or more operational characteristics of a device fabricated from said at least one sample;
(c) a correlator for obtaining a correlation between said operational characteristics and said information; and
(d) a predictor for predicting the operational characteristics of devices fabricated from further samples of said bandgap material, based on said correlation and on information about dislocation defects obtained from said further samples.

In a twelfth aspect, the present invention provides a method for distinguishing dislocation defects from grain boundaries in a multicrystalline silicon wafer, said method including the steps of: capturing a luminescence image of said silicon wafer; capturing a conventional optical image of said silicon wafer; and comparing said luminescence and optical images.

In a thirteenth aspect, the present invention provides a system for distinguishing to dislocation defects from grain boundaries in a multicrystalline silicon wafer, said system including: a first image capture device for capturing a luminescence image of said silicon wafer; a second image capture device for capturing a conventional optical image of said silicon wafer; and a comparator for comparing said luminescence and optical images.

In a fourteenth aspect, the present invention provides a method for monitoring a process for reducing the density of defects in a bandgap material, said method including the steps of:
(a) capturing a photoluminescence image of said material before said process;
(b) processing said image to obtain a first measurement of the density of said defects in said material;
(c) capturing a photoluminescence image of said material after said process;
(d) processing said image to obtain a second measurement of the density of said defects in said material; and
(e) comparing said first and second measurements.

In a fifteenth aspect, the present invention provides a method for controlling a process for reducing the density of defects in a bandgap material, said method including the steps of:
(a) capturing one or more photoluminescence images of said material before said process, or after said process, or both;
(b) processing said images to obtain one or more measurements of the density of said defects in said material; and
(c) adjusting one or more conditions of said process based on said one or more measurements.

In a sixteenth aspect, the present invention provides a system for monitoring a process for reducing the density of defects in a bandgap material, said system including: an image capture device for capturing photoluminescence images of said material before and after said defect reduction process; an image processor for processing said images to obtain measurements of the density of said defects in said material before and after said defect reduction process; and a comparator for comparing said measurements.

In a seventeenth aspect, the present invention provides a system for controlling a process for reducing the density of defects in a bandgap material, said system including: an image capture device for capturing photoluminescence images of said material before and/or after said defect reduction process; an image processor for processing said images to obtain measurements of the density of said defects in said material before and/or after said defect reduction process; and a controller for adjusting one or more conditions of said process based on at least one of said measurements.

BRIEF DESCRIPTION OF THE DRAWINGS

A preferred embodiment of the invention will now be described, by way of example only, with reference to the accompanying drawings in which.

DESCRIPTION OF THE PREFERRED AND OTHER EMBODIMENTS

Lateral variations in the electronic material quality of the substrate material (for example a silicon wafer) can have a large impact on key performance parameters of solar cells manufactured from the material, such as open circuit voltage, short circuit current density, fill factor and efficiency.

The preferred embodiment provides methods and systems that can rapidly assess the quality of raw wafers at the start of solar cell manufacturing or at the end of wafer manufacturing and predict cell performance parameters or statistical variations thereof expected under normal processing conditions. The methods and systems can also be used to assess the effect of additional processing steps, such as annealing, intended to improve the electronic material quality.

The preferred embodiment includes analysis of photoluminescence (PL) images of a bandgap material, i.e. images of band-to-band recombination luminescence generated by photo-excitation of the material. In alternative embodiments the luminescence may be generated by other means, such as electrical excitation (electroluminescence). PL imaging is a fast and contact-less metrology technique for silicon wafer characterisation, disclosed for example in published US patent application 2009/0051914 A1, the contents of which are incorporated by reference. PL imaging can be conducted on as-cut me-silicon wafers with high spatial resolution and a total data acquisition time of about one second per wafer.

The preferred embodiment has particular application to the characterisation of raw or partially processed silicon wafers, including assessing the absolute or relative density distributions of defects such as dislocations, and the subsequent prediction of solar cell parameters including open circuit voltage, short circuit current density, fill factor and efficiency. The present description concentrates on determining the distribution density of dislocations, but the inventive concepts also apply to analysis of other defects that can result in degraded cell performance, including impurities, cracks and shunts.

Based on this information on the defect density distribution a wafer can be classified or priced, with the following benefits:

1) Wafer manufacturers can use the information to assess the quality of their outgoing material (the wafers) so that they can demonstrate to their customers (cell manufacturers) that they delivered wafer quality that meets the specification, or they can price their product according to the product quality;
2) Cell manufacturers can use the information in the opposite way, i.e. to check that the wafers received from the wafer manufacturer meet the required quality specification.
3) Wafer manufacturers can systematically use PL images on raw or partially processed wafers to determine the distribution of dislocations in three dimensions (i.e. across the area of wafers and down through the brick from which the wafers were cut). This information may be fed back into the processing conditions for block casting, to improve the manufacturing process.
4) Cell manufacturers can use wafer binning to sort wafers. Because different optimum processing conditions exist for wafers with variable amounts of dislocations, the wafers may then be processed with optimised bin-specific processing conditions. Further, variations to the processing may be achieved to effect a higher quality outcome, e.g. a wafer may be rotated to ensure that a specific high defect zone is not near the bus bars of an as-completed cell. In modern cell concepts such as semiconductor finger technology where a laser is used to define highly laterally conductive current paths, the laser could be guided to avoid dislocation or impurity-rich regions.
5) Cell manufacturers may also reject wafers with insufficient material quality.
6) Cell manufacturers may also use the wafer binning to assign wafers to specific solar cell processing lines. That assignment can include assigning to different solar cell lines processing the same type of solar cell but with different processing parameters in different lines, or to different cell lines producing different types of solar cells.
7) The defect distribution parameters as determined from a PL image can become standard parameters for wafer quality.
8) Over time, a large database of analysis can be built up so as to provide improved image analysis results and improved algorithms for binning/sorting.

Figure 1A:
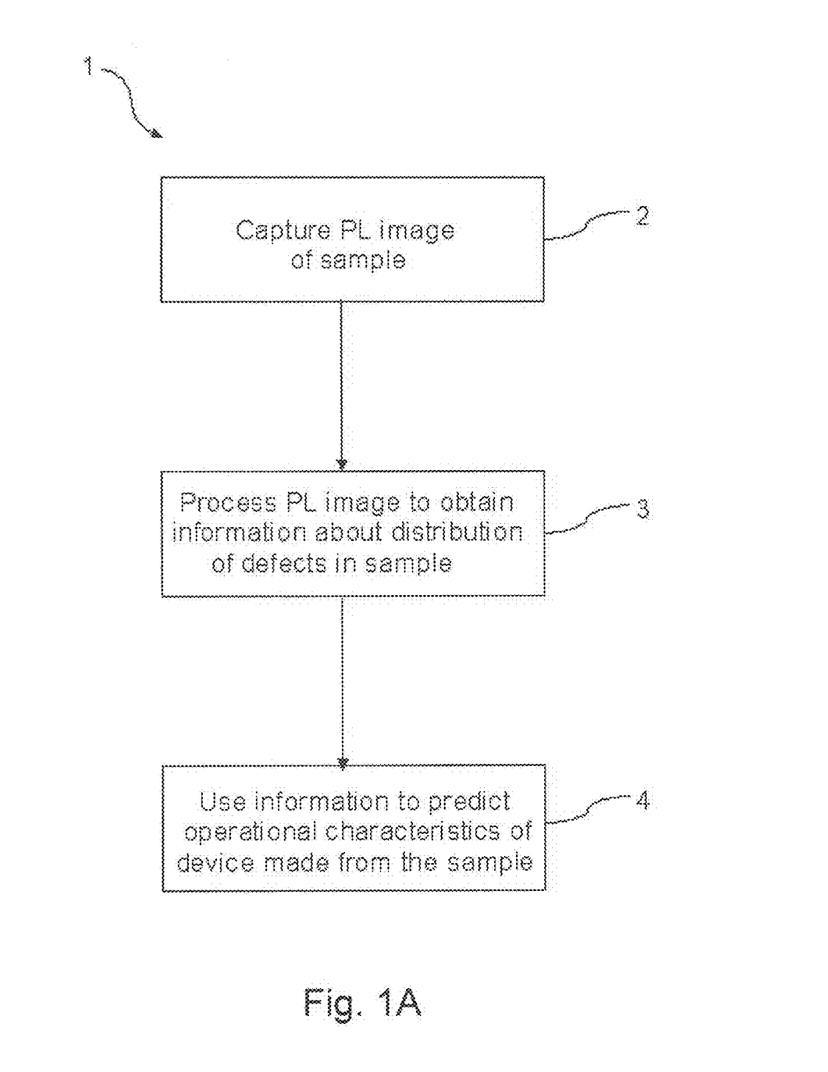
FIG. 1A illustrates the steps in a preferred embodiment.

The steps involved in one preferred embodiment involve the capture and processing of photoluminescence images from bandgap materials such as silicon, and using the results of the processing to predict operational characteristics of devices, such as photovoltaic (solar) cells, fabricated from the materials. The steps 1 are illustrated in FIG. 1A and include a first step 2 of capturing a photoluminescence image followed by processing 3 of the captured image, firstly to enhance the image to highlight those defects such as dislocations, that may be present in the sample, and secondly to obtain information about the distribution of those defects. This information may include an absolute or relative area average of the defect density or a metric that is correlated with the defect density or with the defect distribution or both. Finally, in step 4 the information is used to predict operational characteristics of devices, such as solar cells, made from the material.

Figure 1B:
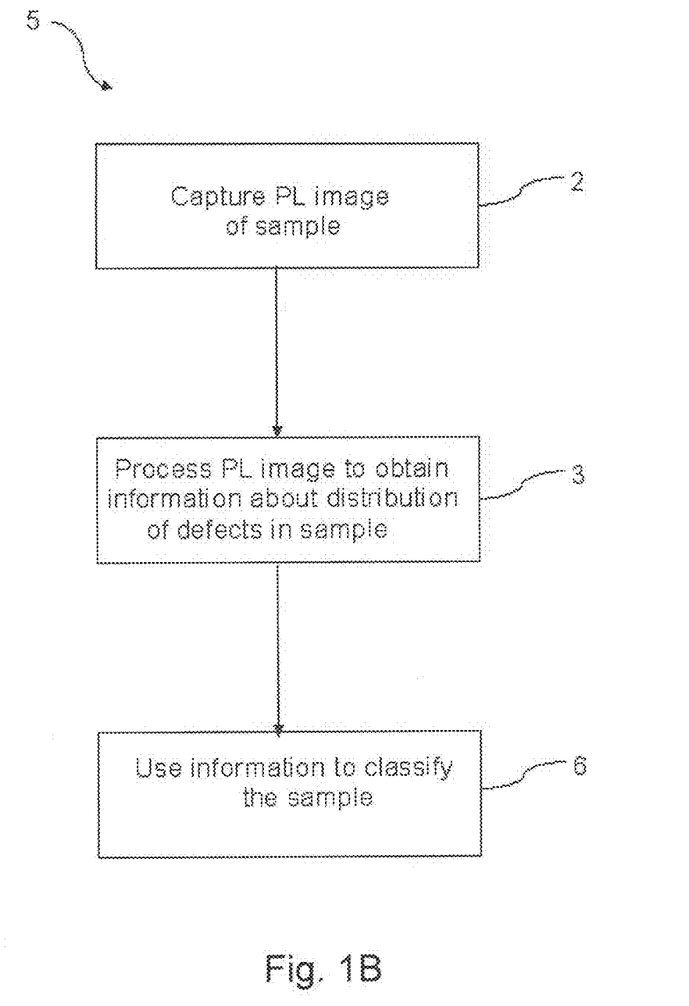
FIG. 1B illustrates the steps in another preferred embodiment.

The steps involved in another preferred embodiment involve the capture and processing of photoluminescence images from bandgap materials such as silicon, and using the results of the processing to classify the materials. The steps 5 are illustrated in FIG. 1B and include a first step 2 of capturing a photoluminescence image followed by processing 3 of the captured image, firstly to enhance the image to highlight those defects such as dislocations that may be present in the sample, and secondly to obtain information about the distribution of those defects. This information may include an absolute or relative area average of the defect density or a metric that is correlated with the defect density or with the defect distribution or both, and is used to assign a figure of merit to the sample. Finally, in step 6 this figure of merit is used to classify the sample, e.g. for binning or pricing purposes. It will be appreciated that while operational characteristics of subsequent devices cannot be predicted with absolute accuracy, it is sufficient for binning or pricing purposes to know that solar cells made from bandgap material with a higher dislocation density will, on average, have inferior properties.

PL image capture is known and is, for example, disclosed in 'Progress with luminescence imaging for the characterisation of silicon wafers and solar cells', 22nd European Photovoltaic Solar Energy Conference, Milano, Italy, September 2007, the contents of which are hereby incorporated by cross reference.

Figure 2:
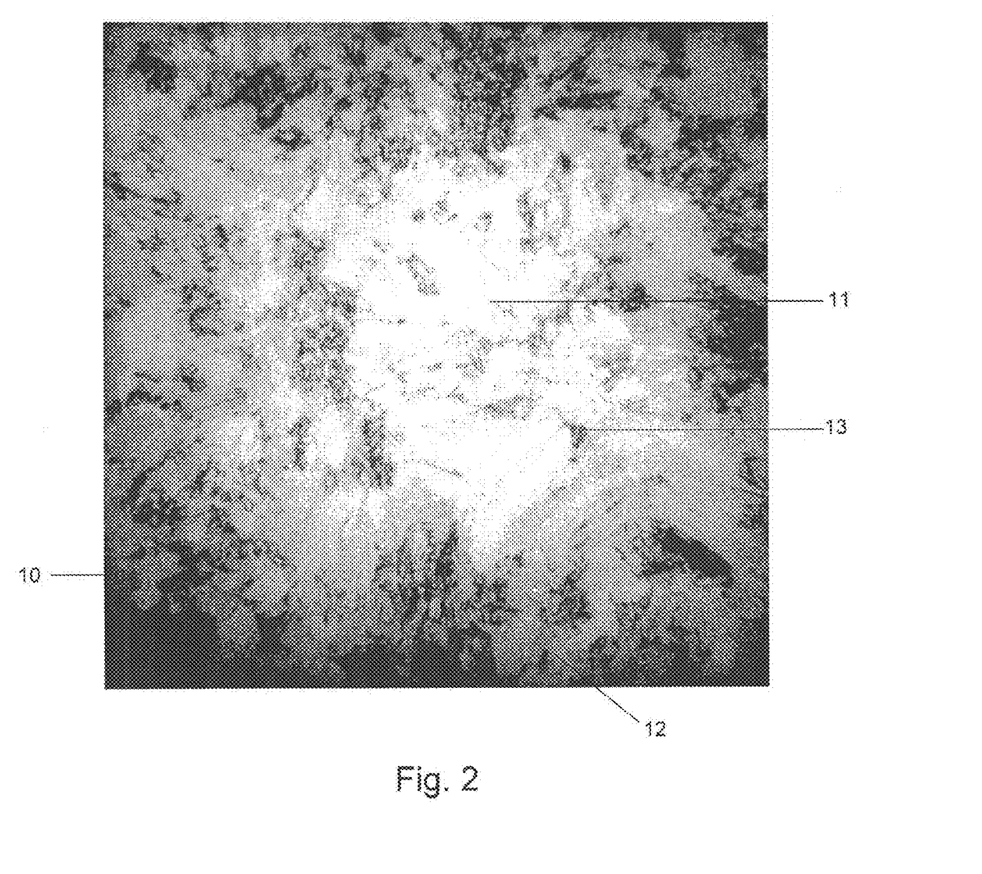
FIG. 2 illustrates a photoluminescence image of a multicrystalline silicon wafer.

FIG. 2 shows an example of a PL image 10 of a 1 Ωcm p-type 15×15 cm² mc-silicon wafer as would be typically used in solar cell manufacturing. This image reveals a strong variation of the material quality, i.e. bright areas 11 correspond to areas with good electronic properties and darker areas 12 correspond to areas with poorer electronic properties. Note that in the PL imaging applications discussed here we refer to measurements of the band-to-band luminescence, which occurs during radiative recombination between electrons in the conduction band and holes in the valence band of a semiconductor. In silicon the majority of photons emitted during that process are in the spectral range 850 nm to 1300 nm at room temperature.

The PL image 10 was taken on an as-cut 15×15 cm² mc-Si wafer. Further analysis discloses that the image has two dominating features: 1) a long range variation with higher luminescence intensity in the centre 11 and lower intensity towards the edges 12; and 2) short range variations 13 of lower intensity. The latter patterns are interpreted as dislocation clusters. Some individual lines may also be caused by recombination-active grain boundaries.

The next step 3 in the method of the preferred embodiment is to process the PL image. A variety of standard image processing techniques exist that allow filtering or enhancing of specific predetermined image features, which in the present application are characteristic for example of certain types of defects that can degrade solar cell performance. Common types of image processing techniques, amongst others, include noise reduction (median filtering, wavelet domain methods, bilateral filtering, grey scale morphological reconstruction), line detection (for example using edge detection techniques such as Sobel-edge detection), and image deconvolution (Weiner filtering, blind deconvolution, iterative deconvolution via the Lucy-Richardson and Landweber method). These techniques are described in standard texts such as 'Digital Image Processing' by R. Gonzalez and R. Woods ($3^{rd}$ ed, 2008).

Figure 3:
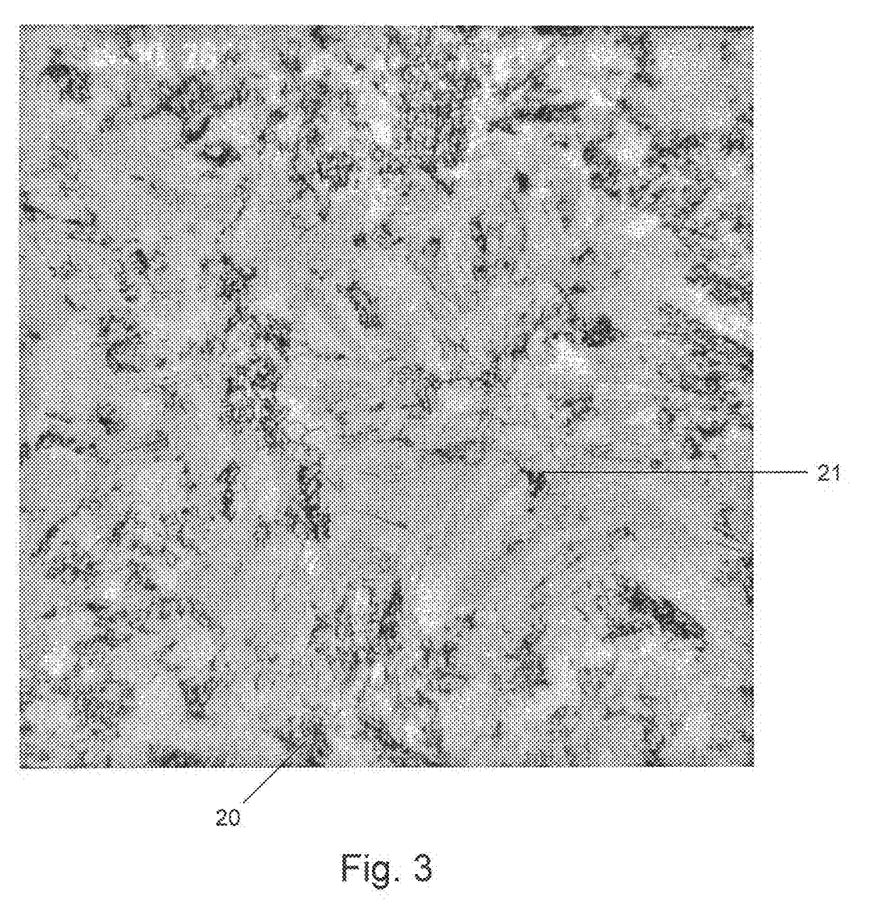
FIG. 3 illustrates a filtered version of the image shown in FIG. 2.

'High pass filtering' is a generic term for a filtering process that removes low frequency components of an image or some other signal or data set. In the present context, high pass filtering can be used to remove the influence of the long range luminescence variations from a PL image. FIG. 3 illustrates an example result 20 of the PL image of FIG. 2 image processed with a high pass filter that eliminates long range variations, so that the distribution of small scale variations 21, caused for example by dislocations or recombination active grain boundaries, is revealed more clearly. By way of example only, a simple form of high pass filtering consists of applying a Fast Fourier Transform (FFT) to the original image, eliminating low spatial frequencies from the resulting frequency domain image, and applying an inverse FFT.

In alternative embodiments, further image processing steps can be applied to the image. In one example, the image itself may be normalised with respect to a background doping level for improved results. The background dopant may for example be boron for p-type silicon or phosphorus for n-type silicon. In another example, image contrast may be enhanced by one of the abovementioned image deconvolution techniques, taking into account a theoretical or experimentally measured point spread function of the system. Point spread effects are generally caused by non-ideal optics, and in the case of luminescence imaging using a CCD camera, can also be caused by lateral scattering of light within the CCD chip. In the context of dislocations, deconvolution algorithms can greatly enhance the image contrast between dislocations or other local features and the background.

Once a PL image has been enhanced, say by a combination of filtering and deconvolution techniques, to highlight dislocations in the material, the image processing may continue with one or more algorithms, such as Sobel-edge detection, for obtaining information about the distribution density of the dislocations.

Distinguishing dislocations from grain boundaries in PL images of mc-silicon can be difficult in practice. Comparison of PL images with conventional optical images can be useful in this context, because optical images show grain boundaries but not dislocations, allowing the two types of feature to be distinguished.

Figure 4:
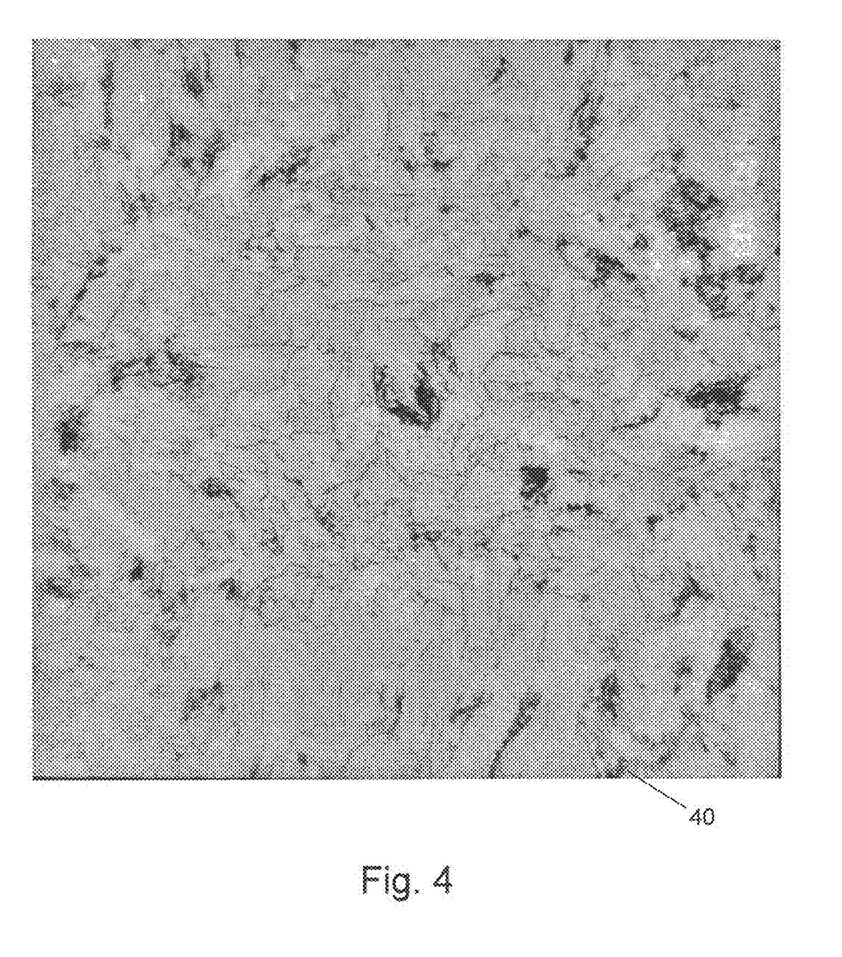
FIG. 4 illustrates a filtered photoluminescence image of a raw multicrystalline silicon wafer.
Figure 5:
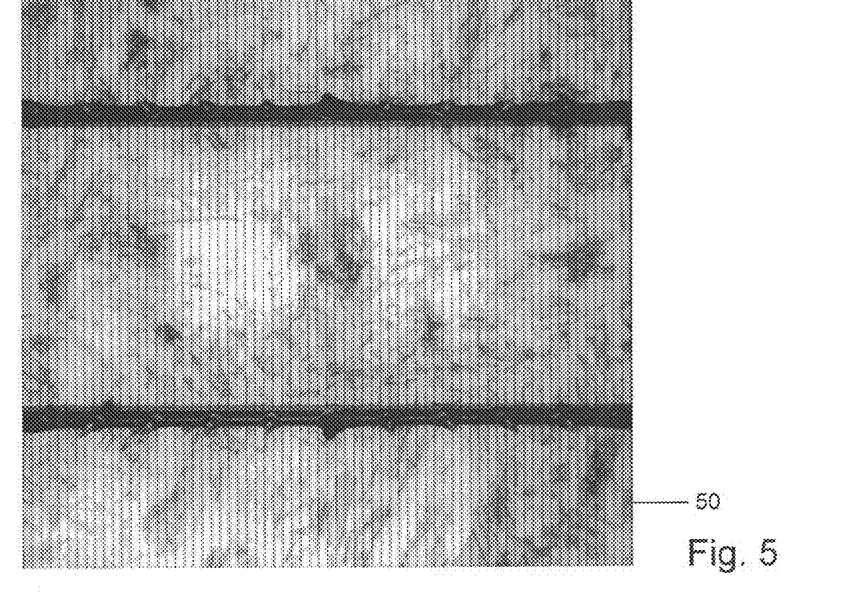
FIG. 5 illustrates a high pass filtered photoluminescence image of a fully processed solar cell made from a wafer adjacent to the wafer of FIG. 4.
Figure 6:
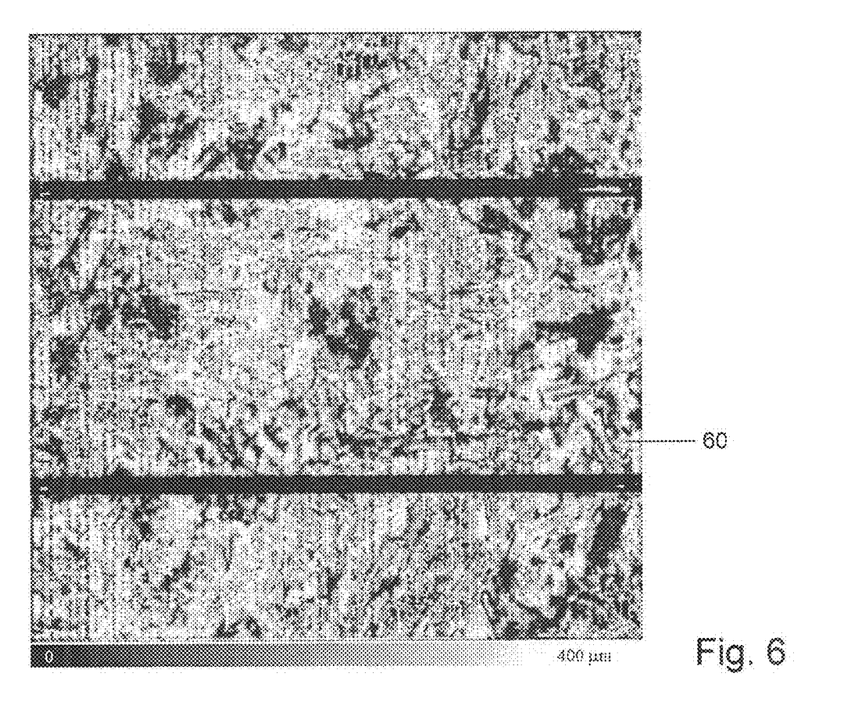
FIG. 6 illustrates a spectral Light Beam Induced Current (LBIC) map of the solar cell of FIG. 5.

Specific defects, particularly dislocations, often appear with very similar spatial distribution in wafers from nearby regions in the same brick, in other words, the spatial distribution varies very little between several neighbour wafers. FIG. 4 shows a PL image 40 of a raw wafer after high pass filtering, FIG. 5 shows a PL image 50 of a finished cell made from a neighbouring wafer, and FIG. 6 illustrates a corresponding diffusion length image obtained from a spectral Light Beam Induced Current (LBIC) map taken on the same cell. A strong correlation is observed between the LBIC data (FIG. 6) and the PL image on the neighbouring raw wafer (FIG. 4). Hence the filtered PL image of a cell can act as a proxy for the LBIC image, and a filtered PL image of a raw wafer can be used as an indicator of the likely operational condition of a cell made from that wafer or from wafers cut from adjacent portions of a brick. This allows performance predictions to be made for a larger sample set, from measurements on only a subset of wafer samples.

Figure 7:
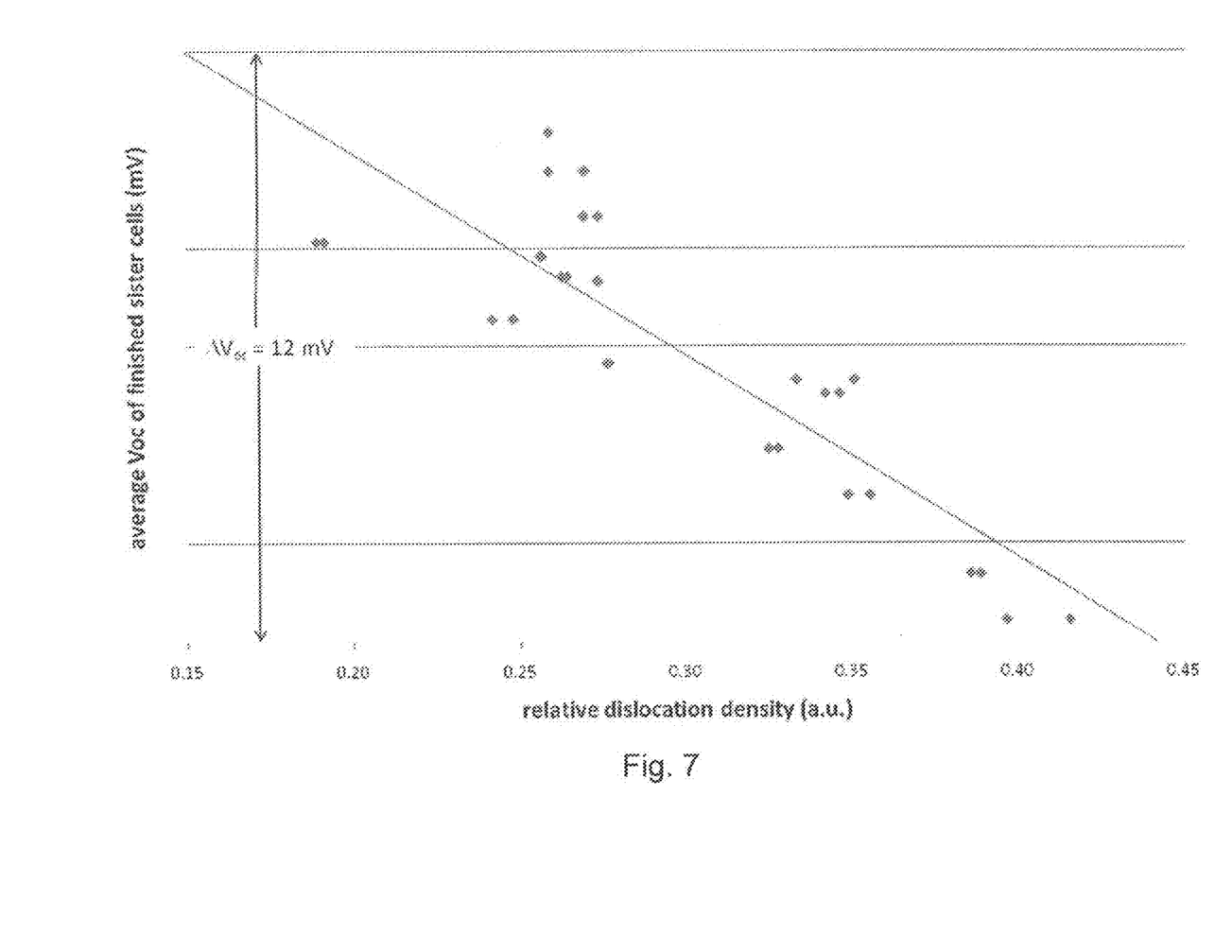
FIG. 7 illustrates a correlation between dislocation density in raw wafers and open circuit voltage in finished cells made from neighbouring wafers.

The LBIC data in FIG. 6 representing regions with low minority carrier diffusion length correspond to regions in which the collection of photo-generated carriers is relatively lower, which tends to have a direct impact on the short circuit current density of the cell. The correlations found between the data of FIG. 4 and FIG. 6 suggest that the PL image on a raw wafer correlates well with the short circuit current density in a finished cell. In a similar fashion, FIG. 7 shows a correlation between the average dislocation density in raw wafers, obtained as described above from PL imaging, and the open circuit voltage of solar cells manufactured from "sister" (neighbouring) wafers. In particular, it can be seen that lower dislocation densities correlate with higher open circuit voltages, so that the dislocation density observed in raw or partially processed wafers can be used to predict cell voltage.

In a simple approach the average absolute or relative density of defected regions (regions with dislocations) across a PL image taken at an early stage of solar cell processing may be correlated with cell parameters such as short circuit current density, open circuit voltage, fill factor or efficiency (as shown in FIG. 7). More sophisticated algorithms can use weighting functions based on the position of the defect, e.g. the proximity to the metal contacts, (e.g. grid lines or busbars) or the edges of the cell. For example a defect that is close to a busbar or one of the metal fingers is likely to have a bigger impact on the cell voltage than a defect that is located further away from the busbar.

The darker a defect appears in a photoluminescence image, the stronger is its recombination activity. A weighting function may also be based on the relative intensity variation of the luminescence intensity in a defected region.

The luminescence intensity is normally proportional to the background doping, which varies in a well known way from the bottom of an ingot to the top. Thus, if the background doping is known (either from the known position of the wafer in the ingot, or via a separate measurement), then the luminescence intensity may be normalised to the doping level, allowing a more quantitative comparison of the luminescence intensity from different wafers. The normalisation can involve dividing the measured luminescence image by a constant factor that is equivalent or proportional to the average background doping concentration across the wafer, itself corresponding in a generally non-linear fashion to the wafer's position in the ingot.

The PL imaging techniques disclosed can not only be used on raw wafers and on finished cells but on wafers at any of the processing stages in solar cell production.

It is known that the density of dislocations in silicon wafers or silicon bricks can be reduced by a thermal annealing process (K. Hartman et al 'Dislocation density reduction in multicrystalline silicon solar cell material by high temperature annealing', Applied Physics Letters vol 93(12) 122108 (2008)). On wafers such a process could be used by wafer manufacturers or by solar cell manufacturers to mitigate the impact of dislocations on cell performance, and wafer manufacturers may also be able to anneal entire bricks. The annealing process could be performed as a batch process or as a continuous in-line process, at a temperature between 1200 and 1400 degrees Celsius. In principle the process can be performed on any type of silicon wafer, but is most useful for silicon samples known to contain dislocations, i.e. multicrystalline silicon wafers (which includes both string ribbon and edge-defined film-fed growth (EFG) wafers) and cast monocrystalline wafers.

Since PL measurements enable rapid assessment of the absolute or relative areal dislocation density and the spatial distribution of dislocation affected areas (i.e. the absolute or relative distribution of dislocation densities), PL imaging can be used to monitor this thermal annealing process. For example PL imaging performed on a sample before and after annealing would allow quantitative assessment of the efficacy of the annealing process. If individual sample tracking is not possible, an analysis could be performed based on statistical data for dislocation densities from a number of samples, calculated from PL images obtained before and after the annealing step.

Such process monitoring could also result in improved process control, where the annealing conditions are adjusted based on the results from PL image analysis. This process control could be performed automatically, based on predetermined algorithms or empirical data. These annealing conditions may for example be the temperature profile (heating the sample to a desired temperature, keeping it at one or more constant temperatures and finally cooling the sample to room temperature), or the atmosphere in the annealing furnace. Optimal process conditions for annealing may also depend on the dislocation density itself, so that the results of a pre-anneal PL measurement may be used to determine optimal annealing conditions. This may be combined with sorting wafers into separate quality bins to allow processing individual bins with given annealing conditions.

A PL image measured prior to an annealing may also be used to classify wafers into wafers with low dislocation density versus wafers with high dislocation density, allowing selection of wafers with low dislocation density which do not require the annealing step, thereby reducing the total amount of wafers that have to go through the additional annealing step and resulting in optimised operation in wafer or cell production.

While PL imaging of band-to-band recombination luminescence is our preferred method for analysing the distribution density of dislocations in silicon, it is not the only method. Under certain processing and excitation conditions, dislocations in silicon have been demonstrated to emit light in the 1400 nm 1700 nm spectral range (I. Tarasov et al, 'Defect passivation in multicrystalline silicon for solar cells', Applied Physics Letters vol 85(19), 4346-4348 (2004)). According to a generalisation of Kirchhoff's law, which is applicable to luminescence, any material that has the ability to absorb light in a specific wavelength range can also emit light in that same range, and vice versa. Dislocation-rich regions in a silicon wafer should therefore absorb more strongly in the 1400 nm-1700 nm spectral range than regions with zero or low dislocation density. In one embodiment, reflectance or transmission measurements limited to that spectral range are used to identify dislocations in silicon. These reflectance or transmission measurements can be performed in a spatially resolved fashion using line-scan or area cameras that are sensitive in the 1400 nm-1700 nm spectral range, in combination with suitable narrow spectrum or suitably filtered light sources.

Apart from dislocations, another example of a specific type of defect that can be identified in starting wafer material (i.e. as-cut wafers) by luminescence imaging are impurity-related defects near the edge of a wafer that result in low carrier lifetime and therefore reduced cell efficiency. As-cut multicrystalline wafers often have low material quality around the edges or in the corners, originating from high impurity concentrations at the bottom, top and side walls of the cast multicrystalline block from which the wafers were cut. These impurities often arise from diffusion of oxygen and transition metals or other metals from the crucible walls into the silicon block during the casting and crystallisation process. At the top of a block, the low carrier lifetime is caused by segregated impurities such as transition metals and carbon which 'float' to the top during the crystallisation, which normally proceeds from the bottom of a block to the top. These low carrier lifetime regions at the bottom, top and sides of a block are normally cut off by the wafer manufacturer before the block is chopped up into bricks, so that ideally only good quality regions are used for wafer production. Often however wafer manufacturers do not cut off enough material, so that very low carrier lifetime material is found in some wafers near an edge or near one corner.

Figure 8:
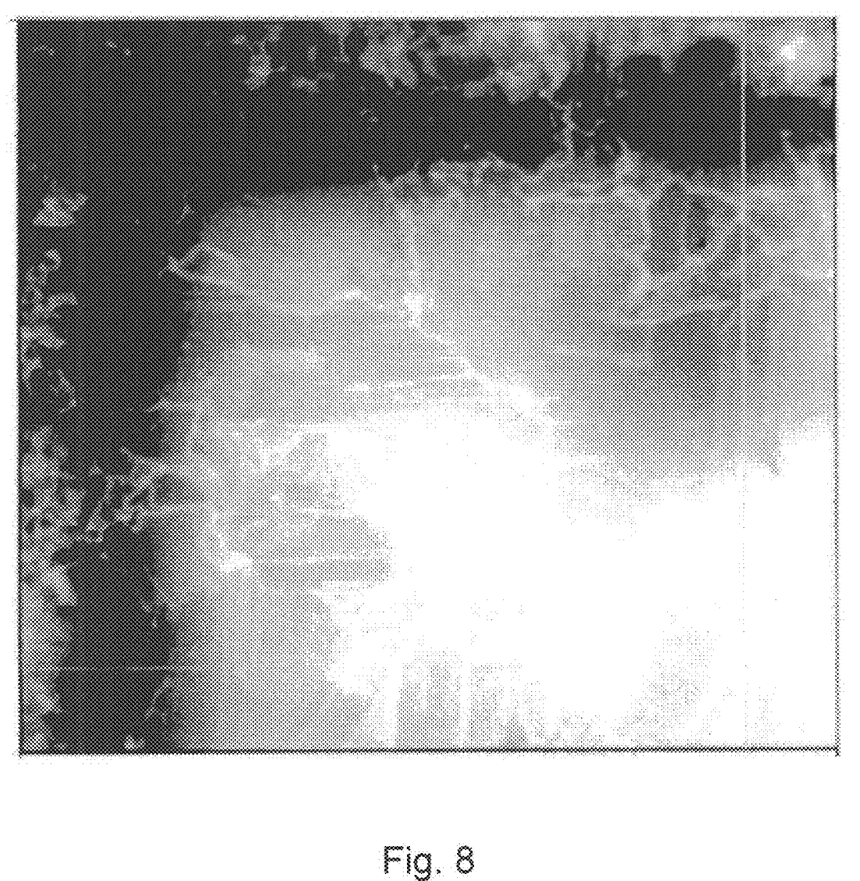
FIG. 8 illustrates a photoluminescence image of a 'boundary' wafer, i.e. a wafer cut from a region close to the edge of an ingot.

FIG. 8 illustrates an example PL image of a wafer that was cut from the edge of a block (left). In the high impurity/low lifetime regions, which appear generally dark in the PL image, defects such as dislocations and grain boundaries appear brighter instead of darker. This contrast reversal occurs because of gettering of impurities by the dislocations, which improves the material quality in their vicinity. These 'bright' dislocations appear more diffused than the 'dark' dislocations of low impurity regions, but similar line detection algorithms can still be used to highlight the dislocations and measure their areal density.

In certain embodiments, the PL imaging can thus be used to identify
1) Wafers from the bottom or top of an ingot.
2) Wafers from the edge or corners of an ingot.

Image processing of the PL images can result in the automatic identification and classification of certain features. Classification may be based for example on the severity of the defect, the latter detectable for example in PL images by the luminescence intensity, or on the affected area, or combinations thereof. Wafer and cell manufacturers may thus use PL imaging to sort these wafers out or bin them into various quality bins, and cell manufacturers can reject such wafers and send them back to the wafer manufacturer or pay a lower price.

Figure 9:
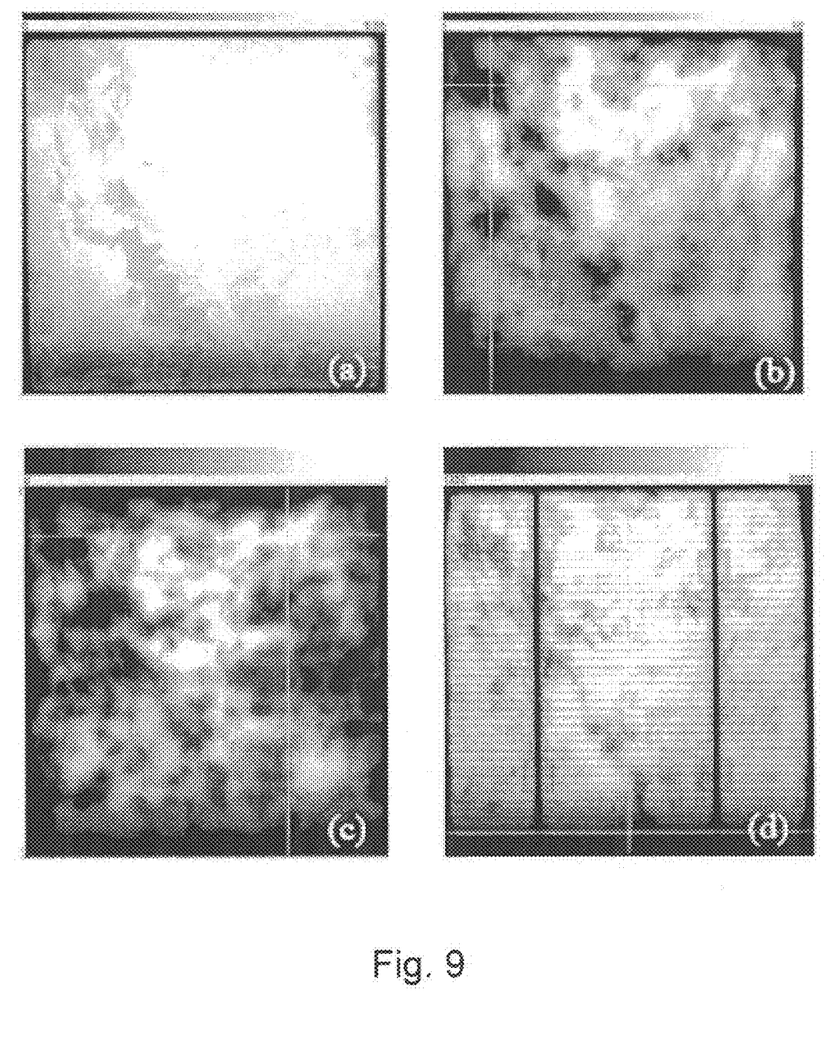
FIG. 9 illustrates photoluminescence images of neighbouring wafers to the wafer of FIG. 8.

An example is shown in FIG. 9, where four neighbouring wafers were PL imaged (a) after surface damage etch, (b) after emitter diffusion, (c) after SiN deposition and (d) after full cell processing. The dislocation clusters that are visible in the finished cell (d) are clearly observed after the diffusion step (b). While the dislocations are also detectable by PL on as-cut wafers, measuring after the diffusion step can be advantageous as the PL intensity is generally enhanced after that step allowing shorter data acquisition, lower quality equipment or resulting in higher spatial resolution images or any combination thereof. The enhanced photoluminescence signal is a result of the field effect surface passivation on the emitter diffused side.

In one embodiment the binning and sorting and dedicated processing procedures may be applied after the emitter diffusion step. Further, it is possible to adjust the processing steps, such as the firing conditions, based on the results from the PL images after the diffusion step, thereby providing improved end results.

Further modifications are possible. Wafer manufacturers could for example use the PL imaging technique not just on wafers but on entire blocks or on the individual square columns (bricks). For example every brick could be measured with PL imaging on one or more sides before it is sawn into wafers, allowing the wafer manufacturer to identify the position of low lifetime regions or to detect dislocation densities on the sides of the bricks, thereby gaining information about the dislocation density inside the ingot at a given height (i.e. at a specific wafer position) or about the position of low lifetime regions as caused by high impurity content. Combining several images will allow acquisition of more detailed and accurate information in that context. Wafer manufacturers may also measure the entire block to identify the best position to chop off the impurity-rich sides, bottom and top.

When a 'brick' from which wafers are sliced is measured, speed is not as crucial as for measuring individual wafers. Normally, a brick is sawn into a few hundred wafers so that there is more time available for characterisation. A line scanning PL tool can therefore be employed where the illumination is in a line shape and a linear detector array is used to capture the emission. Alternatively a series of two-dimensional images can be taken on various parts on the ingot or block in a mapping-style arrangement, thereby generating a high resolution image of the entire ingot or block.

Figure 10:
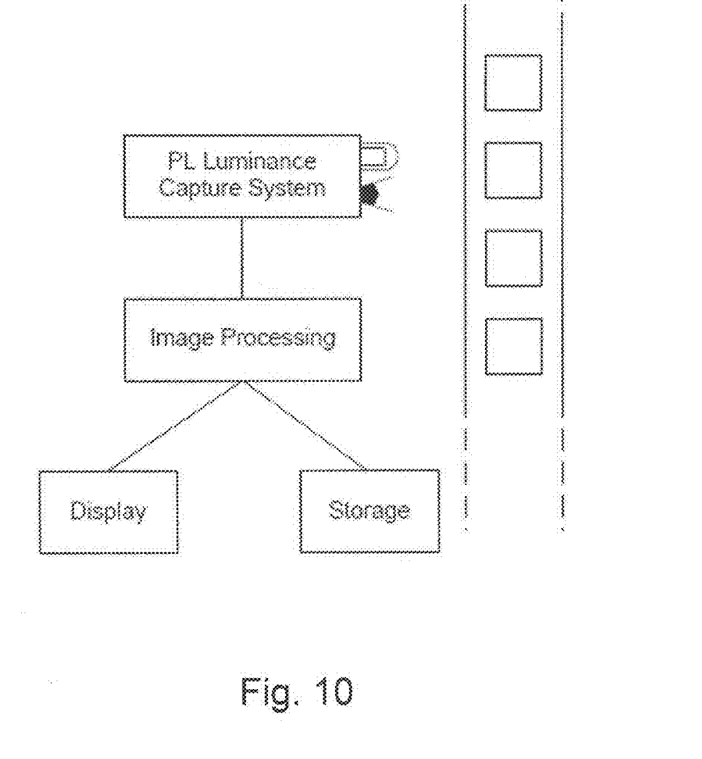
FIG. 10 illustrates a production line process for utilisation of the preferred embodiment.

Turning to FIG. 10, there is illustrated schematically an example production line system for the manufacture of solar cells utilising the method of the preferred embodiment. In this system wafers are transported along a belt where they are imaged by a PL capture system. The resulting images are processed and analysed before display and storage.

The utilisation of the preferred embodiments can be extended to both monocrystalline and multicrystalline wafers. Multicrystalline wafers are normally manufactured using a casting process. Different methods exist for manufacturing monocrystalline silicon wafers, including the 'Czochralsky method' (Cz) and the 'float zone' method. In terms of cell efficiencies, monocrystalline silicon is generally preferable over multicrystalline silicon, however the higher solar cell efficiencies are normally offset by the higher cost of producing monocrystalline wafers. Recently a method for manufacturing cast monocrystalline silicon wafers has been introduced and details of the method can be found in United States Patent Application Publication 2007/0169684 A1 in the name of Stoddard et al. A general advantage of conventional monocrystalline silicon wafers is that they have lower impurity concentrations compared to multicrystalline wafers and can be essentially free from structural defects such as dislocations or grain boundaries. In contrast dislocations can be present in the above mentioned cast monocrystalline wafers. The techniques of the preferred embodiment have equal application to unpassivated cast monocrystalline silicon wafers. Further, the density of structural defects as determined from a wafer by luminescence imaging at an early stage may be correlated with the current density and/or voltage or other cell parameters. In comparison with multicrystalline wafers the identification of the structural defects from luminescence images is significantly easier and more reliable in the case of a cast monocrystalline silicon wafer due to the absence of many other features commonly observed in luminescence images taken on multicrystalline wafers.

The preferred embodiment has direct application to other photovoltaic cell materials and can be utilised with other bandgap materials such as monocrystalline silicon, thin film silicon, CdTe, amorphous silicon, micro-morph silicon, nanocrystalline silicon on glass, copper indium gallium diselenide (CIGS) and related thin film materials.

Although the invention has been described with reference to specific examples it will be appreciated by those skilled in the art that the invention may be embodied in many other forms.

We claim:

1. A method of classifying a plurality of silicon wafers for photovoltaic cell manufacture, said method comprising the steps of:
   (a) capturing a photoluminescence image of a whole silicon wafer of each of said plurality of silicon wafers for photovoltaic cell manufacture;
   (b) processing each of said images to obtain information about defects in each of said plurality of silicon wafers;
   (c) utilizing said information about defects obtained from said photoluminescence image of a whole silicon wafer to apply a classification to said silicon wafer as a whole for each of said plurality of silicon wafers; and
   (d) using said classification to bin each of said silicon wafers into different quality categories based on predicted operational characteristics of photovoltaic cells manufactured from said silicon wafers,
   wherein said processing step obtains information that includes the area sum or area average of dislocation densities in each of said plurality of silicon wafers.

2. The method according to claim 1, further comprising the step of performing the method on one or more wafers cut from adjacent or nearby slices of an ingot or block of silicon, and interpolating or extrapolating the results to predict the operational characteristics of photovoltaic cells manufactured from one or more neighboring wafers cut from said ingot or block, or to apply a classification to said neighboring wafers.

3. The method according to claim 1, further comprising the step of locating low material quality regions caused by edge defects or impurities along an edge of a silicon wafer.

4. The method according to claim 1, further comprising the step of utilizing the classification or predicted operational characteristics to alter parameters associated with a series of processing steps in the formation of a photovoltaic cell so as to improve the quality of said photovoltaic cell.

5. The method according to claim 4, wherein said parameters include the conditions for firing a metal pattern into a silicon wafer.

6. The method according to claim 4, wherein said parameters include the diffusion conditions for diffusing materials into a silicon wafer, or parameters for any other process that creates doped regions in a silicon wafer.

7. The method according to claim 1, further comprising the step of normalizing each said photoluminescence image with regard to the background doping level of each of said silicon wafers.

8. The method according to claim 1, wherein said area sum or area average of dislocation densities is weighted for the location of said dislocations relative to the grid lines or other metallic contacts of a photovoltaic cell to be manufactured from a silicon wafer.

9. The method according to claim 1, wherein said area sum or area average of dislocation densities is weighted according to the severity of said dislocations.

10. The method according to claim 9, wherein said severity is assessed based on relative intensity variations in a photoluminescence image.

11. The method according to claim 1, further comprising the step of obtaining information about dislocation defects in each of said plurality of silicon wafers by using microwave photoconductance decay, optical transmission, or optical reflection measurements.

12. The method according to claim 11, wherein said optical transmission or optical reflection measurements are performed in the 1400 nm-1700 nm spectral range.

13. The method according to claim 1, wherein said operational characteristics include open circuit voltage, short circuit current density, fill factor or efficiency.

14. The method according to claim 1, wherein the classification of said plurality of silicon wafers includes rejecting or pricing of said silicon wafers.

15. A system for classifying a plurality of silicon wafers for photovoltaic cell manufacture, said system comprising:

a photoluminescence capture system for generating and capturing a photoluminescence image of a whole silicon wafer of each of said plurality of silicon wafers;

an image processor for processing each said photoluminescence image to obtain information about defects in each of said plurality of silicon wafers; and a classifier for utilizing said information about defects obtained from said photoluminescence image of a whole silicon wafer to apply a classification to said silicon wafer as a whole for each of said plurality of silicon wafers and for using said classification to bin each of said silicon wafers into different quality categories based on predicted operational characteristics of photovoltaic cells manufactured from said silicon wafers, wherein the image processor obtains information that includes the area sum or area average of dislocation densities in each of said plurality of silicon wafers.

16. The method according to claim 1, wherein said processing step obtains information that includes the relative distribution of dislocations in each of said plurality of silicon wafers.

17. The method according to claim 16, wherein said relative distribution of dislocations is weighted for the location of said dislocations relative to the grid lines or other metallic contacts of a photovoltaic cell to be manufactured from a silicon wafer.

18. The method according to claim 16, wherein said relative distribution of dislocations is weighted according to the severity of said dislocations.

19. The method according to claim 18, wherein said severity is assessed based on relative intensity variations in each said photoluminescence image.

20. The method according to claim 1, further comprising the step of using the wafer binning to sort said plurality of silicon wafers for photovoltaic cell manufacture.

* * * * *